US008865470B2

(12) United States Patent
Yan et al.

(10) Patent No.: US 8,865,470 B2
(45) Date of Patent: Oct. 21, 2014

(54) INSTRUMENT SETUP SYSTEM FOR A FLUORESCENCE ANALYZER

(71) Applicant: Becton, Dickinson and Company, Franklin Lakes, NJ (US)

(72) Inventors: Ming Yan, Pleasanton, CA (US); Alan M. Stall, Encinitas, CA (US); Joseph T. Trotter, La Jolla, CA (US); Robert A. Hoffman, Livermore, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 30 days.

(21) Appl. No.: 13/787,460

(22) Filed: Mar. 6, 2013

(65) Prior Publication Data

US 2014/0087394 A1 Mar. 27, 2014

Related U.S. Application Data

(63) Continuation of application No. 12/616,001, filed on Nov. 10, 2009, now Pat. No. 8,415,161.

(60) Provisional application No. 61/252,001, filed on Oct. 15, 2009, provisional application No. 61/199,312, filed on Nov. 13, 2008.

(51) Int. Cl.
| *G01N 31/00* | (2006.01) |
| *G01N 21/64* | (2006.01) |
| *G01N 21/76* | (2006.01) |

(52) U.S. Cl.
CPC ........ *G01N 21/6486* (2013.01); *G01N 21/6428* (2013.01); *G01N 2021/6421* (2013.01); *G01N 2021/6441* (2013.01); *G01N 2201/121* (2013.01); *Y10S 435/967* (2013.01)
USPC ................. 436/8; 436/10; 436/164; 436/171; 436/172; 422/82.05; 422/82.08; 435/287.1; 435/967

(58) Field of Classification Search
None
See application file for complete search history.

(56) References Cited

U.S. PATENT DOCUMENTS

| 5,093,234 | A | * | 3/1992 | Schwartz ...................... 435/7.21 |
| 6,897,954 | B2 | * | 5/2005 | Bishop et al. ................. 356/317 |
| 2004/0121483 | A1 | | 6/2004 | Corson et al. | |

FOREIGN PATENT DOCUMENTS

| JP | 2002-501184 A | 1/2002 |
| JP | 2004-205508 A | 7/2004 |
| JP | 2010-156679 A | 7/2010 |

OTHER PUBLICATIONS

Vogt et al. Fluorescence Intensity Calibration for Immunophenotyping by Flow Cytometry, Methods 21: 289-296 (2000).*
"Anti-Mouse Ig, k/Negative Control (BSA) Compensation Plus (7.5 μm) Particles Set", Technical Data Sheet, BD™ CompBeads Plus (2008).
"Anti-RAT Ig, k/Negative Control (FBS) Compensation Particles Set", Technical Data Sheet, BD™ CompBeads (2008).
"BD Cytometer Setup and Tracking Beads", One3-ml, vial—Catalog No. 641319, Three3-ml, vial—Catalog No. 642412, Jun. 2007.
BD FACSDiva™ 6.0 Software, "Robust Statistics in BD FACSDiva™ 6.0 Software", BD Bioscience Tech Note, Sep. 2007.
Baumgarth et al., "A practical approach to multicolor flow cytometry for immunophenotyping", Journal of Immunological Methods, vol. 243; 77-97 (2000).
Gaigalas et al., "The Development of Fluorescent Intensity Standards", Journal of Research of the National Institute of Standards and Technology, vol. 106 (2): 381-389 (2001).
Gaigalas et al., "Quantitating Fluorescence Intensity From Fluorophores: Assignment of MESF Values", Journal of Research of the National Institute of Standards and Technology, vol. 110 (2): 101-114 (2005).
Henderson et al., "Terminology and Nomenclature for Standardization in Quantitative Fluorescence Cytometry", Cytometry, vol. 33: 97-105 (1998).
Schwartz et al., "Standardizing Flow Cytometry: A Classification System of Fluorescence Standards Used for Flow Cytometry", Cytometry, vol. 33: 106-114 (1998).
Schwartz et al., "Quantitating Fluorescence Intensity from Fluorophore: The Definition of MESF Assignment", Journal of Research of the National Institute of Standards and Technology, vol. 107 (1): 83-91 (2002).
"Sphero™ Calibration Particles", Spherotech, Inc. 27845 Irma Lee circle, Unit 101, Lake Forest, IL 60045 (2007).
Stall, Allan, "QR and Br in BD FACSDiva v6 Software: Parameters for Characterizing Detector Performance", Application Notes, BD Bioscience (2008).
Vogt et al., "Fluorescence Intensity Calibration for Immunophenotyping by Flow Cytomertry", Methods, vol. 21: 289-296 (2000).
Wang et al., "Quantitating Fluorescence Intensity From Fluorophores: Practical Use of MESF Values", Journal of Research of the National Institute of Standards and Technology, vol. 107 (4): 339-353 (2002).

* cited by examiner

*Primary Examiner* — Gail R Gabel
(74) *Attorney, Agent, or Firm* — Bret E. Field; Bozicevic, Field & Francis, LLP

(57) ABSTRACT

The present invention reagents and methods for setting up an instruments having a multiplicity of detector channels for analyzing a multiplicity of fluorescent dyes. The present invention is particularly applicable in the field of flow cytometry.

11 Claims, No Drawings

INSTRUMENT SETUP SYSTEM FOR A FLUORESCENCE ANALYZER

CROSS REFERENCE TO RELATED APPLICATIONS

This application claims priority to U.S. provisional application No. 61/252,001, filed Oct. 15, 2009, and U.S. provisional application No. 61/199,312, filed Nov. 13, 2008, and is a continuation of application Ser. No. 12/616,001, issued as U.S. Pat. No. 8,415,161, the disclosures of which are incorporated herein by reference.

BACKGROUND OF THE INVENTION

1. Field of the Invention

The present invention relates to instruments for analyzing a multiplicity of fluorescent dyes using a multiplicity of photodetectors. The present invention is particularly applicable to the field of cytometry, more particularly, flow or scanning cytometry.

2. Description of Related Art

Particle analyzers, such as flow and scanning cytometers, are well known in the art. In these systems, fluorescently labeled particles, such as molecules, analyte-bound beads, or individual cells, are individually analyzed by exposing each particle to an excitation light, typically one or more lasers, and measuring the resulting fluorescence from each of dye labels. Each particle may be labeled with a multiplicity of spectrally distinct fluorescent dyes. Typically, detection is carried out using a multiplicity of photodetectors, one for each distinct dye to be detected. Both flow and scanning cytometers are commercially available from, for example, BD Biosciences (San Jose, Calif.).

Other instruments systems are known to be capable of detecting a multiplicity of fluorescent dyes using a multiplicity of photodetectors. For example, nucleic acid amplification reaction products from multiple target sequences can be detected and distinguished using fluorescently labeled probes, wherein each target-specific probe is bound to a spectrally distinct dye. Typically, an instrument for analyzing nucleic acid amplification products measures the total fluorescence from a reaction mixture, and the frequency of each target species is determined from the measured fluorescence from each dye.

In flow cytometers and other instruments that employ a multiplicity of photodetectors to detect a multiplicity of dyes, the collected light is separated into specific ranges of wavelengths, typically by a system of frequency-dependent filters and dichroic minors, such that the light detected by a particular photodetector is limited to a predefined range of wavelengths, referred to as a detection channel. The detection channels and dyes are selected such that the peak of the emission spectrum of each dye is within the frequency range of a different detection channel, i.e., each detection channel detects primarily the emission from a single dye. However, because of the breadth of the emission spectra of fluorescent dyes, typically a dye will fluoresce in more than one detection channels and, thus, measurements of dye fluorescence are not independent. The emission of one dye in detection channels intended for the detection of other dyes is referred to by a number of terms, such as spillover, fluorescence spectral overlap, and crosstalk.

Methods of decreasing the effect of spillover or crosstalk on the dye fluorescence measurements are known in the art. Such methods involve adjustment of the signal measured by each photodetector by an amount calculated to compensate for the contribution from dyes other than the primary dye to be detected. Examples in the field of flow cytometry include Bagwell, C. B.; Adams, E. G. "Fluorescence Spectral Overlap Compensation for any Number of Flow Cytometer Parameters", Ann. N.Y. Acad. Sci. 677, 167-184 (1993); Roederer, M. et al., "Eight Color, 10-Parameter Flow Cytometry to Elucidate Complex Leukocyte Hetrogeneity", Cytometry29, 328-339 (1997); and Bigos et al., 1999, Cytometry 36: 36-45, each incorporated herein by reference. Commercially available data analysis software packages, such as WinList™ (Verity Software House, Topsham, Me.), Flow Jo (TreeStar, Inc., Ashland, Oreg.), and FCS Express (De Novo Software, Los Angeles, Calif.) enable software compensation on the stored data files produced by a flow cytometer. See also the whitepaper describing the BD FACSDiVa™ Option for the BD FACSVantage SE Flow cytometer (BD Biosciences, San Jose, Calif.; available at "www" followed by "bdbiosciences.com"), incorporated herein by reference.

In a typical flow cytometric analysis, labeled particles suspended in a liquid medium are passed through a narrow channel one at a time past an interrogation region. Particles are labeled with one or more fluorescent dyes to facilitate identification. While passing the interrogation region, labeled particles are exposed to excitation light, typically from one or more lasers, and the resulting particle fluorescence is measured. Typically, the amount of excitation light scattered by the particles also is measured. The amount of scattered light and the intensity of emitted fluorescent light from each of the bound labels provide a characterization of the labeled particles. Flow cytometry provides a rapid means of analyzing a large number of particles and, importantly, provides data on each individual particle, rather than only on the particle population as a whole. However, the detection of low level of light emitted by the dye molecules bound to a single particle typically requires amplification of the detected signal. To detect such low levels of emitted light, current flow cytometers use photodetectors such as photomultiplier tubes (PMT) and avalanche photodiodes (APD) that are capable of amplifying the signal by a factor of $10^6$ or greater. The amplification gain of a PMT or APD can be varied by adjusting an input voltage to the detector, or by adjusting the gain of a downstream amplifier, or both.

Instruments for the detection of labeled nucleic acid amplification products typically measure labeled products at the population level, rather than at the level of individual particles, and the degree of signal amplification required depends on the volume of sample analyzed. Signal amplification, if used, can be achieved using an amplifier in-line with the detector output. As with a PMT or APD, the amplification gain typically is adjustable.

Prior to carrying out a particular assay using a flow cytometer, photodetector signal amplification (gain) and the signal range detected are adjusted based on the brightness/amount of dyes to be detected in order that the sample measurements are within the dynamic range of the detection system. To provide maximum resolution of sample fluorescence level, it is desirable that the photodetector gain and the detected signal range are set such that the expected range of sample fluorescence spans a significant portion of the detectable range. As the expected range of sample fluorescence is sample-specific, these instrument parameters must be determined and set prior to analyzing each kind of sample. In addition, these parameters are specific to the instrument, as individual instruments will differ in their performance.

Photodetector gain and the detected signal range typically are set in a flow cytometer by analyzing samples of standards that are representative of the unknown sample to be analyzed subsequently. For example, before analyzing a cell-containing sample, a sample of beads or cells dyed with an amount of dye representative of the expected brightness of a brightly dyed cell is used to set the upper end of the detection range, or a sample of unlabeled beads or cells that fluoresce at a level of an unlabeled sample cell are used to set the lower end of the detection range. This determination of appropriate settings typically is carried out each day, even if the same type of analysis is to be carried out each day, in part because of day-to-day variation in instrument and photodetector performance.

Because the levels of photodetector gain in each of the multiple photodetectors affects the measurement of light in each channel, the amount of spillover fluorescence measured is dependent on the photodetector gains. Using current flow cytometers, the relative amounts of spillover fluorescence from each of the dyes are experimentally determined after the photodetector gain settings have been chosen. Any change to the instrument's photodetector gain settings after the initial setup renders the measurements of spillover and, hence, the compensation, no longer applicable to current instrument settings. Typically, after any change to the instrument's photodetector gain settings, the spillover from the dyes is re-determined experimentally using the current instrument settings.

U.S. Pat. No. 6,897,954, incorporated herein by reference, describes instruments for analyzing a multiplicity of fluorescent dyes using a multiplicity of amplifying photodetectors, such as flow cytometers, that are capable of automatically resetting the instrument parameters, including the spillover and compensation values, following a change in photodetector amplification. To enable recalculation of parameters following a change in photodetector amplification, the instruments stores representations of the pairwise functional relationships between measured fluorescence and signal amplification of the photodetector (photodetector gain) for each of the photodetectors and for each of the fluorescent dyes.

SUMMARY OF THE INVENTION

The present invention provides method and reagents for determining spillover and compensation values, and predicting fluorescent reagent fluorescence emission (brightness), for use with instruments for analyzing a multiplicity of fluorescent dyes using a multiplicity of photodetectors. The methods use predetermined "calibrated spillover" values, defined herein, to simplify the setup of the instrument. These calibrated spillover values are predetermined for each fluorescent reagent labeled with a different fluorescent dye from the fluorescence emissions measured from the dye in each detector channel, calibrated using the fluorescence emissions of a "broad-band" reference material that emits in each of the channels. During instrument setup, spillover or compensation values applicable to the particular instrument settings to be used in an assay, which may be different than those used to obtain the predetermined calibrated spillover or compensation values, are obtained by measuring the fluorescence emissions of the same or equivalent reference material under the particular instrument settings, and calculating the reagent spillover or compensation values from the measured reference material emissions and the predetermined calibrated spillover or compensation values. Similarly, the expected brightness of a fluorescent reagent having a predetermined calibrated fluorescence emission value is obtained by measuring the fluorescence emission of the reference material under the particular instrument settings, and calculating the expected reagent brightness from the measured reference material emissions and the predetermined calibrated reagent brightness.

Calibrated spillover values of a fluorescent dye are obtained from fluorescence emissions from the dye measured in a secondary (spillover) channel and in the primary channel by calibrating each emission value using the fluorescence emission of a reference material measured in the corresponding detector channel, both measured under the same instrument settings. The calibrated spillover values of the present invention are independent of the photodetector gains, unlike directly measured, uncalibrated spillover values used to determine compensation. This gain-independence allows the calibrated spillover values to be obtained at any time prior to setting up the instrument for a particular assay, using photodetector gain settings that may be significantly different from those used for the final assay.

Compensation of data measured during an assay requires uncalibrated spillover values that are specific to the particular photodetector gain settings used in the assay. In the methods of the present invention, these uncalibrated spillover values are obtained by measuring the fluorescence emission in each of the detector channels of the reference material under the photodetector gain settings to be used in the assay, and calculating the uncalibrated spillover values from the predetermined calibrated spillover values and the fluorescence emissions measured from the reference material. Compensation values are then obtained from the spillover values. This simplifies instruments setup for the end user as only the reference material needs to be analyzed under the assay-specific instrument photodetector gain settings.

Uncalibrated fluorescence intensity (brightness) values of assay reagents can be useful to help set photodetector gain settings such that data obtained from the reagents will be "on-scale" or within the instrument's dynamic range. The brightness of an assay reagent under a given photodetector gain setting is estimated by the gain-dependent, uncalibrated fluorescence measurement obtained from the predetermined gain-independent, calibrated fluorescence measurement and the fluorescence of the reference material measured under the given photodetector gain setting. This aspect of the invention can be used to set photodetector gain settings such that a reagent's brightness matches a predetermined target brightness value. During instrument setup, the photodetector gain is re-adjusted after measuring the reference material such that the expected brightness of the reagent matches the target value. A predetermined target value, specific for each lot of manufactured reagent, can be provided by the reagent manufacturer to simplify instrument setup.

The reference material consists of one or more populations of particles that, taken together, emit in each of the detection channels (hence, "broad-band"). In a preferred embodiment, the reference material consists of a single population of microparticles dyed with multiple fluorescent dyes, such that each microparticle emits in each of the detection channels. Alternatively, the reference material may comprise multiple populations, each stained with one of more fluorescent dyes. The fluorescence of the different populations can be measured independently either by analyzing the populations separately, or by combining the populations and analyzing the mixture. Using a flow cytometer, for example, microparticles from different populations can be distinguished by appropriate gating based on the measured intensities or scatter properties.

The present invention enables a number of useful novel features that are particularly advantageous for the commercial production and distribution of fluorescent reagents, such as flow cytometry reagents. These novel features include the following.

The calculation of compensation for any given set of photodetector gain settings can be obtained from the measurement of only the reference material under the given photodetector gain settings.

The recalculation of compensation after changing one or more photodetector gain settings can be obtain from the measurement of only the reference material under the new settings.

The setting of a PMT gain to obtain a desired brightness for a particular reagent, such that data obtained from the reagent will be "on-scale" or within the instruments dynamic range, can be obtained from the measurement of only the reference material. Predetermined target brightness values can be provided along with the reagent, in addition to the calibrated fluorescence values, to facilitate instrument setup.

The calibrated emission values for each dye in a multiplex assay, which are used to obtain the calibrated spillover values, can be determined at different times and under different photodetector gain settings. For each dye, the calibrated values are obtained from the fluorescence of the dye and fluorescence of the reference material measured under the same photodetector gain settings, but the photodetector gain settings used to obtain calibrated values for one dye do not need to be the same as those used for another dyes. This aspect of the invention simplifies combining dyed reagents for use in a multiplex assay.

The substitution of a new dye for one of the dyes of an existing set of dyes used in a multiplex assay requires only the measurement of calibrated emission values for the new dye, which are obtained from the fluorescence of the new dye and fluorescence of the reference material measured under the same photodetector gain settings. These photodetector gain settings do not need to be the same settings used to obtain calibrated values for each of the other dyes. This aspect of the invention simplifies the substitution of a dye in a multiplex assay.

The substitution of a new reagent lot for a previous reagent lot is simplified. A new reagent lot may have different spillover values, in some cases, significantly so. Calibrated spillover values obtained for the new reagent lot enable direct substitution of the new lot for the old lot without needing to further revalidate the reagent lot.

The substitution of a new reference material, or lot of the same reference material, is simplified. Calibrated emissions of the new reference material with respect to the old reference material enable direct calculation or recalculation of both calibrated and uncalibrated reagent emission and spillover values with respect to the new reference material. Thus, the substitution of a new reference material or lot of reference material does not require recalculation of the calibrated spillover values for the assay reagents.

In a preferred embodiment, the instrument is a cytometer, more preferably, a scanning or flow cytometer. However, the present invention is applicable to any instrument for analyzing a multiplicity of fluorescent dyes in a multiplicity of detector channels, in which compensation is desired, i.e., wherein spectral overlap of the dye emission spectra results in one or more of the detector channels measuring light from more than one dye. Although the present invention is most applicable to instruments that have gain-adjustable photodetectors, e.g., photomultiplier tubes (PMT), the present invention is also applicable to instruments that have photodetectors with preset gain or no gain. In general, instruments designed to have unadjustable photodetector gain will still exhibit instrument to instrument variation in photodetector response that affects the compensation required. Furthermore, as an instrument ages, it is expected that the photodetector response may change over time, which may affect the compensation required.

DETAILED DESCRIPTION OF THE INVENTION

The following definitions are provided for clarity. Unless otherwise indicated, all terms are used as is common in the art. All reference cited herein, both supra and infra, are incorporated herein by reference.

As used herein, "system" and "instrument" are intended to encompass both the hardware (e.g., mechanical and electronic) and associated software (e.g., computer programs) components.

The present invention is most applicable to instruments that have multiple photodetectors, each having an adjustable signal amplification, also referred to as gain. It is not critical whether the photodetector gain is provided by a photodetector alone or by a signal amplifier that amplifies the output of the photodetector. For this reason, "photodetector" is used herein to refer to either a photodector alone or a photodetector with accompanying signal amplifier(s), if present. For example, the signal from a photodiode, which has a fixed intrinsic response, or a avalanche photodiode, which has an adjustable amplification, but which typically used at a fixed amplification level, may be passed through either a linear or logarithmic signal amplifier providing an adjustable gain; the photodetector gain in this case refers to the amplification provided by the combination of the photodiode and the signal amplifier. In preferred embodiments, photomultiplier tubes are used, which provide signal amplification. However, additional amplification of the photodectector output may be used. For example, in the BD FACSDiVa™ Option for the BD FACSVantage™ SE Flow cytometer (both from BD Biosciences, San Jose, Calif.), the signals from the photomultiplier tubes are passed through a pre-amplifier before being converted to a digital signal by an analog-digital converter.

The signal amplification (gain) of the photodetector is adjusted during instrument setup by adjusting one or more parameters. For example, the input voltage level of a PMT is a parameter that is used to set the signal amplification of a PMT, and is the parameter that is adjusted during instrument setup. As another example, in the case that photodiodes or avalanche photodiodes are connected to a downstream adjustable amplifier, the parameter that is used to set the signal amplification of the downstream amplifier is the parameter that is adjusted during instrument setup. For convenience, the value of the parameter that is used to set the photodetector gain will be referred to interchangeably as the photodetector gain, as is customary in the art. Thus, for example, the input voltage of a PMT (or, simply, the PMT voltage) will be used as the measure of PMT gain.

Although the present invention is most applicable to instruments that have gain-adjustable photodetectors, the present invention is also applicable to instruments that have photodetectors with preset gain or no gain. In general, instruments designed to have unadjustable photodetector gain will still exhibit instrument to instrument variation in photodetector response that affects the compensation required. Furthermore, as an instrument ages, it is expected that the photodetector response may change over time, which may affect the compensation required. The present methods are equally suited for determining the required compensation in each case.

A "detector channel", "detection channel", or "channel" refers to the range of wavelengths that is detected by a specific photodetector. Typically, a plurality of non-overlapping detector channels are measured to facilitate the independent measurement of a plurality of spectrally distinct fluorescent dyes. The range of wavelengths detected typically is determined by the use of frequency-dependent filters and/or dichroic minors, as is well known in the art. For clarity, the use herein of the term "channel" is distinguished from a secondary use in the field of flow cytometry to refer to a discrete subdivision of the range of intensity values detectable by a single detector.

Typically, dyes and detector channels are selected such that, as much as is feasible, the emission maximum of each dye is within a different detector channel, i.e., such that each dye is matched to a detector channel optimized to detect light from that dye. However, due to the breadth of its emission spectrum, light from a given dye may be emitted within one or more other detector channels. The light emitted by a dye within a detector channel other than the detector channel that most closely matches the emission maxima of the dye is referred to herein as "spillover".

The detector channel that most closely matches the emission maximum of a dye is referred to herein, with reference to the given dye, as the dye-detection channel or primary channel. All other detector channels are referred to, with reference to the given dye, as spillover channels or secondary channels. A dye and its dye-detection channel will be referred to as "corresponding" or "matched." With reference to a detection channel, the dye that corresponds to the detection channel is referred to as the primary dye; other dyes that emit spillover into the detection channel are referred to as secondary dyes.

It will be understood that the correspondence of a primary dye and a detector channel depends on the set of dyes being used in the assay and the detector channels used. Typically, in a multiplex assay, each dye is measured in a particular primary detector which measures light over a distinct range of wavelengths. However, in some embodiments, primary detectors for two different dyes may measure light over overlapping, or even identical, ranges of frequencies if the dyes emissions are spatially separable. For example, as using an instrument having multiple excitation sources, such as a flow cytometer having multiple excitation lasers focused on spatially separate regions of the flow stream, separate sets of detectors are used to measure the fluorescence emitted after excitation with each of the lasers. With such instruments, dyes having different stokes shifts, such that the dyes have similar emission spectra, but different excitation spectra, that are excitable using different lasers may be used.

As used herein, the term "particles" refers to both to synthetic particles, such as microparticles or beads, and to particles derived from biological sources, such as eukaryotic cells, bacteria, viruses, or macromolecules.

As used herein, the terms "microparticles", "microbeads", and "beads" are used interchangeably. These terms refer to small particles with a diameter in the nanometer to micrometer range, typically about 0.01 to 1,000 μm in diameter, preferably about 0.1 to 100 μm, more preferably about 1 to 100 μm, and, for use in flow cytometry, typically about 1 to 10 μm. Microparticles can be of any shape, but typically are approximately spherical ("microspheres"). Microparticles are typically synthetic particles, but can also be derived from biological particles, such as eukaryotic cells, bacteria, viruses, or macromolecules.

As used herein, a "population" of particles refers to a group of particles that possess essentially the same optical properties with respect to the parameters to be measured, such as cells of the same type (cell population), or synthesized beads that, within practical manufacturing tolerances, are of the same size, shape, and composition (bead population). Beads can consist of particles of any shape and need not be spherical.

The term "MFI", as used herein, refers to the mean or median fluorescence intensity of a population of fluorescence particles. It will be understood that other statistical measures of the population fluorescence, such as truncated mean or truncated median fluorescence, may be used.

Reference Material

A "reference material", as used herein, refers to any substance that can be used to establish a known relationship between a measurement response and a value of the substance being measured. Reference materials are standards that have a known fluorescence property that can be used to establish an instrument's response to a material having the known property.

In the present methods, the measured fluorescence of a dye or dye-labeled particle in a given detection channel is calibrated using the measured fluorescence of a reference material that emits in each of the detector channels, also referred to herein as a broad-band reference material. A reference material may contain a fixed, but unknown, number of dye molecules per particle, which is sufficient for measuring relative fluorescence values, or may contain a known number of dye molecules, in which case the reference material further enables calculating the fluorescence per dye molecule.

The reference material consists of one or more populations of particles that, taken together, emit in each of the detection channels. In a preferred embodiment, the reference material consists of a single population of microparticles dyed with multiple fluorescent dyes, such that each microparticle emits in each of the detection channels. Alternatively, the reference material may comprise multiple populations, each stained with one of more fluorescent dyes. The fluorescence of the different populations can be measured independently either by analyzing the populations separately, or by combining the populations and analyzing the mixture. Using a flow cytometer, for example, microparticles from different populations can be distinguished by appropriate gating based on the measured intensities or scatter properties.

Microparticles for use as a reference material can be made of any appropriate material (or combinations thereof), including, but not limited to polymers such as polystyrene; polystyrene which contains other co-polymers such as divinylbenzene; polymethylmethacrylate (PMMA); polyvinyltoluene (PVT); copolymers such as styrene/butadiene, styrene/vinyltoluene; latex; or other materials, such as silica (e.g., $SiO_2$).

Microparticles suitable for use in the present invention are well known in the art and commercially available from a number of sources. Unstained microparticles in a variety of sizes and polymer compositions that are suitable for the preparation of fluorescent microparticles are available from a variety of sources, including: Bangs Laboratories (Carmel, Ind.), Interfacial Dynamics Corporation (Portland, Oreg.), Dynal (Great Neck, N.Y.), Polysciences (Warrington, Pa.), Seradyne (Indianapolis, Ind.), Magsphere (Pasadena, Calif.), Duke Scientific Corporation (Palo Alto, Calif.), Spherotech Inc. (Libertyville, Ill.), and Rhone-Poulenc (Paris, France). Chemical monomers for preparation of microparticles are available from numerous sources.

Fluorescent dyes have been incorporated into microparticles in a variety of ways, including, for example, by copolymerization of the dye into the microparticles during manufacture (U.S. Pat. No. 4,609,689 to Schwartz et al. (1975), U.S. Pat. No. 4,326,008 to Rembaum (1982), both incorporated by reference); by entrapment of the fluorescent dye into the microparticles during the polymerization process; or by non-covalent incorporation of the fluorescent dye into previously prepared microparticles (U.S. Pat. Nos. 5,326,692; 5,723,218; 5,573,909; 5,786,219; and 6,514,295; each incorporated by reference). The method of labeling the microparticles is not a critical aspect of the invention; any method that allows the labeling of the microparticles with a controllable amount of dye can be used.

In a preferred embodiment, fluorescently labeled microparticles are prepared by bath dying according to well-known methods. Bath dyeing methods are described, for example, in U.S. Pat. Nos. 5,326,692; 5,723,218; 5,573,909; 5,786,219; and 6,514,295. Such microparticle prepared by bath dying methods are also referred to as hard-dyed beads.

In a preferred embodiment, the reference material consists of a single population of microparticles dyed with multiple fluorescent dyes, such that each microparticle emits in each of the detection channels. Commercially available beads dyed with multiple fluorescent dyes and designed to emit in multiple detector channels include BD™ Cytometer Setup and Tracking beads (CS&T beads, BD Biosciences, San Jose, Calif.), and Rainbow and Ultra Rainbow alignment beads and calibration particles from Spherotech, Inc., Lake Forrest, Ill.).

BD™ Cytometer Setup and Tracking beads are polystyrene beads dyed with a mixture of fluorescent dyes. The beads emit fluorescence in detector channels over a range of 400 to 800 nm, which encompasses the range typically used in BD digital flow cytometers for measuring the emission from a variety of commonly used fluorescent dyes, including, for example, Indo 1, DAPI, Hoechst, Pacific Blue™, AmCyan, Qdot 655, Qdot 700, Alexa Fluor® 405, FITC, PE, PE-Texas Red®, PerCP, PerCP-Cy™5.5, PE-Cy™7, PE, PE-Texas Red®, PerCP, PerCP-Cy5.5, PE-Cy7, APC, APC-Cy7, APC-HL 750, Alexa Fluor® 700. The beads are useful as a reference material for calibrating the emission from any of the listed fluorescent dyes, or other fluorescent dyes that are detectable using these or similarly defined detection channels. As provided, the BD Cytometer Setup and Tracking beads consist of a mixture of equal concentrations of bright (3 μm), mid (3 μm), and dim (2 μm) beads, each bead dyed with a mixture of fluorochromes. For use in the present invention as a reference material, only beads of a single emission intensity are used. The different bead populations can be distinguished by their size and intensity.

In an alternative embodiment, the reference material may comprise multiple populations, each stained with one of more fluorescent dyes. For example, the reference material may comprises a set of reference populations, one for each detector channel, each labeled with the primary dye for that detector channel. To calibrate fluorescence emissions in a plurality of detection channels, the set of reference populations is used, such that for each channel, the emissions in that channel are calibrated by the emission from the reference particle labeled with the primary dye for that channel. Commercially available sets of beads, each dyed with a single dye, include BD FACS™ 7-color setup beads and BD Calibrite™ beads, both available from BD Biosciences (San Jose, Calif.).

BD FACS 7-color setup beads include separately packaged bead populations, each either unlabeled or labeled with one fluorophore each. Collectively, the bead populations are labeled with the following dyes: fluorescein (FITC); R-phycoerythrin (PE); peridinin chlorophyll protein (PerCP); PerCP cyanine 5.5 tandem (PerCP-Cy™5.5); PE cyanine 7 tandem (PE-Cy7); allophycocyanin (APC); or APC cyanine 7 tandem (APC-Cy7). BD Calibrite™ beads (BD Biosciences, San Jose, Calif.) include beads labeled with FITC, beads labeled with PE, beads labeled with PerCP, and beads labeled with APC.

Although synthetic microparticles dyed with multiple dyes are preferred, reference particles can be made using other particle types, including biological particles. For example, the reference materials may consist of populations of cells stained with dye-labeled antibodies specific to a cell surface marker that is expressed at a consistent level, such that the cells become labeled with a consistent average number of antibodies bound per cell. For each given detection channel, a reference population is prepared corresponding to the channel by staining a sample of the cells with an antibody labeled with the primary dye for that channel. Thus, a reference material that consists of a set of reference populations, one corresponding to each detection channel, is produced by separately staining samples of cells with an antibody labeled with a primary dye for one of the detection channels.

In general, the reference material may comprise particles of any type that contain, or are labeled with, a consistent number of dye molecules per particle, and are suitable for being measured using the instrument. For use with a flow cytometer, a variety of cell-based or synthetic bead-based particles can be used. The reference material typically is used multiple times in the present methods, initially to calibrate measured spillover values, and subsequently to calculate uncalibrated spillover values from the earlier-determined calibrated spillover values. As considerable time may elapse between uses of the reference material, stability or reproducibility of the fluorescence emissions of the reference material is a desirable property.

Fluorescence-Matched Standards

As described more fully below, spillover values and other fluorescence properties of a dye-labeled assay reagent typically are determined empirically using a standard particle labeled with the same dye. In general, the emission spectrum and, hence, the spillover, of a dye is altered when the dye is conjugated to a detection reagent or used to label a particle, and the actual spillover of the dye when used in the assay may differ from the spillover determined using a standard particle. It is desirable to use a standard particle that exhibits fluorescence properties that closely approximate the fluorescence properties of the dye when used in the assay, i.e., when bound to an antibody that is, in turn, bound to a cell and under the final assay conditions. Standard particles that are designed to exhibit fluorescence properties that closely approximate the fluorescence properties of the dye-labeled assay reagents are referred to herein as "spectrally matched" or "fluorescence-matched" standards. Such standards are well known in the art. Examples include fluorescence-matched standards made from dyed-labeled synthetic beads or from stained cells.

Fluorescence-matched standards made from dye-labeled synthetic microparticles have been widely used. For example, standard particles consisting of hard-dyed beads and standard particles consisting of synthetic beads coated with an antigen to which dye-labeled antigen-specific antibodies are bound have been used. Hard-dyed beads have the advantage of exhibiting stable fluorescence properties, but the measured spillover may not closely represent the actual spillover from the dye used under the assay conditions. Standard particles consisting of synthetic beads coated with an antigen to which dye-labeled antigen-specific antibodies have been bound may more closely match the assay reagents, as in both cases the dye is bound to an antibody. However, the use of a synthetic microparticle coated with an antigen, rather than a cell that expresses the antigen, still may result in measured spillover values that differ from the spillover exhibited under the final assay conditions.

To more closely match the fluorescence properties of the a dye-labeled assay reagent, as used in an assay, it is preferable to use fluorescence-matched standards consisting of populations of stained cells, wherein the cells are stained by labeling an expressed cell-surface antigen with an antigen-specific antibody labeled with the dye. A set of fluorescence-matched standards, one for each of the different fluorescent dyes used in a multiplex assay, are produced by separately staining samples of the cells with the same antibody, but labeled with a different one of the dyes.

In a more preferred embodiment, the fluorescence-matched standards consist of $CD4^+$ lymphocytes in fixed whole blood, preferably human, labeled with a dye-labeled CD4-specific antibody. A set of fluorescence-matched standards is produced using different batches of the CD4-specific antibody, each batch labeled with a primary dye for one of the detection channels. Because whole blood is readily available, the use of fixed whole blood in the preparation of fluorescence-matched standard s enables the end user to independently produce fluorescence-matched standards that are equivalent to the fluorescence-matched standards used to obtain the predetermined calibrated spillover values.

An advantageous feature of using fluorescence-matched standards consisting of $CD4^+$ lymphocytes in fixed human blood, labeled with dye-labeled CD4-specific antibodies, is the consistency of the expression level of CD4. A careful analysis using and PE-labeled anti-CD4 antibodies and BD Quantibrite™ standards (BD Biosciences, San Jose, Calif.) shows that there are approximately 40,000 antibodies bound per $CD4^+$ lymphocyte in fixed human blood, and that this number is consistent between samples. This consistent level of CD4 expression on $CD4^+$ lymphocytes in fixed human blood enables the creation of fluorescence-matched standard particles that contain a consistent number of dye molecules and, thus, exhibit a consistent brightness level. This property of the standards allows a fluorescence intensity value to be assigned to the particles.

To produce $CD4^+$ lymphocyte-based standard particles that provide a consistent fluorescence intensity level, the anti-CD4 antibodies are labeled with a consistent average number of dye molecules per antibody. As described below, the fluorescence intensity level can be used to provide an arbitrary, but fixed, measure of the fluorescence intensity of a reagent. For this purpose, the actual number of dye molecules per antibody, typically characterized as the dye-to-protein ratio, is not critical. Furthermore, fluorescence-matched standard particles used to measure the emissions of different dyes need not be labeled with antibodies having the same number of dye molecules per antibody.

Compensation

Compensation refers to the process of effectively removing from the total amount of light detected within a detector channel the contribution due to spillover from dyes other than the primary dye, i.e., the contribution from the secondary dyes. Thus, after compensation, the amount of light detected from a single detector channel represents a measure of the light emitted by a single dye, specifically, the primary dye. Compensation facilitates analysis of the data from multiply dyed particles by making the measurements of each of the dyes independent.

To help in understanding the invention, the general principles of compensation are described for an instrument having n channels for detecting n dyes. It is assumed that the n channels and n dyes are numbered such that the primary detection channel for each dye has the same number as the dye (e.g. channel 2 is used to detect dye 2). So numbered, spillover is the dye fluorescence measured by a detector channel having a different number. This numbering scheme is chosen for convenience and elegance of presentation and is not a critical aspect to the invention.

Let $O_i$ denote the total fluorescence measured (observed) in the ith detector channel, which is the sum of the individual flourescences measured from each dye. Let $D_j$ denote the fluorescence of dye j measured in detector j, i.e., the fluorescence measured by the matched detector channel. Then the fluorescence of the jth dye measured in the ith channel can be written as $(S_{ij} \cdot D_j)$, where $S_{ij}$, referred to as a spillover coefficient, is the relative fraction of $D_j$ detected in channel i. By definition, $S_{ii}=1$. The total fluorescence measured in the ith detector channel can be written as $$O_i = \Sigma S_{ij} \cdot D_j, \quad (1)$$

where the summation is over the n dyes detected. Equation (1) provides a system of n equations, one for each detector channel.

Compensation is used to determine the fluorescence of each dye in its matched dye-detector channel (each $D_j$) from the total fluorescence measured in each channel, which includes contributions from dye spillover. Compensation is carried out by simultaneously solving the system of equations for the $D_j$. It should be noted that, in a system without spillover, wherein the emission of each dye is detected only by its dye-detection channel, equation (1) simplifies to $O_i = D_i$ for all i, and no compensation is necessary.

For compactness, the above system of equations, and the mathematics of compensation correction, are described herein using matrix algebra. However, it will be clear that this representation is for convenience and clarity of presentation and that other representations of the system of equations may be used and are equivalent. In particular, it will be clear that a software implementation need only carry out equivalent calculations, but that the details of a software implementation are not a critical aspect of the invention.

Let O be the n×1 column vector of fluorescence measurements in each of the n channels, i.e., $O=[O_1, \ldots O_n]^T$. O represents the vector of observed, uncompensated measurements. Let D be the n×1 column vector of dye fluorescence for each of the n dyes, i.e., $D=[D_1, \ldots D_n]^T$. D represents the vector of compensated measurements. Let S be the n×n matrix of spillover coefficients, S. Then, the system of equations represented by equation (1) can be written in matrix form as $$O = S \cdot D \quad (2)$$

and the compensated fluorescence values, D, are obtained by left-multiplying both sides of the above equation with the inverse of the spillover matrix, $$S^{-1} \cdot O = D. \quad (3)$$

The inverse of the spillover matrix is called the compensation matrix.

The spillover matrix can be estimated by measuring the fluorescence of a single dye in each detector channel, and repeating this for each dye. The measurements of the same dye, typically measured using a fluorescence-matched standard, in each detector channel correspond to one column of the spillover matrix. The fluorescence measurements in each column are normalized by dividing by the fluorescence measured in the primary detection channel to obtain the relative spillover coefficients. Given the ordering of the channels and dyes chosen, the resulting spillover matrix has ones on the diagonal ($S_{ii}=1$) and the off-diagonal coefficients correspond to the relative spillover into the detector channels intended for the measurement of different dyes.

In the above description of compensation, it is assumed that the fluorescence of each dye is measured directly. However, in some embodiments, particularly wherein the instrument is a flow cytometer, only particles within a given size range are measurable and dye molecules must be bound to a particle of a suitable size to be measurable. In practice, the fluorescence of a dye is measured in a flow cytometer using a fluorescence-matched standard that consists of bead or cell population labeled with a uniform amount of dye and measuring the fluorescence of the fluorescence-matched standard. However, the unlabeled beads or cells may fluoresce in one or more of the detector channels. This fluorescence of unlabeled beads or cells, referred to as autofluorescence, raises the background level of fluorescence detected in each channel. The autofluorescence can be determined by measuring the fluorescence of an unlabeled particle population in each detector channel. To obtain an accurate estimate of the true fluorescence from each dye, the autofluorescence from the particle to which the dye is bound can be subtracted from the measured fluorescence intensities before the spillover matrix is estimated. Compensation taking into account autofluorescence is described in U.S. Pat. No. 6,897,954, incorporated herein by reference. In flow cytometry, autofluorescence typically is ignored during the acquisition of data from samples.

To facilitate discussions of the spillover matrix, because the coefficients within a single column of the spillover matrix correspond to the fluorescence measured from the same population of dyed particles in each of the channel, a single column of the spillover matrix will be referred to as corresponding to a particular dye. Similarly, because the coefficients within a single row of the spillover matrix correspond to the fluorescence measured from the different populations of dyed particles in a single channel, a single row of the spillover matrix will be referred to corresponding to the photodetector. The compensation matrix will be referred to in the same manner. Thus, the same column in the compensation matrix and spillover matrix will be referred to as corresponding to the same particular dye, and the same row in the compensation matrix and spillover matrix will be referred to as corresponding to the same particular photodetector.

Measuring Spillover Values

Typical methods for setting up a flow cytometer include an empirical determination of the spillover values (coefficients) for each dye, determined after the photodetector gains have been set. In practice, this empirical determination typically is made using fluorescence-matched standards designed to closely approximate the fluorescence properties of the dyes, as used in the assay. Where clear from context, the spillover from a dye and the spillover of a dye as measured using a particle or bead population uniformly labeled (stained) with the dye will be used herein interchangeably.

To determine the spillover values for a given dye, the fluorescence of a sample of a population of particles uniformly labeled with the dye is measured in a each detection channel. The dye's spillover value into a secondary detection channel is calculated as the ratio of the measured emission of the labeled particles in the secondary channel to the measured emission in the primary channel, i.e., the ratio of the MFI of the labeled particles in the secondary channel to the MFI in the primary channel.

Using the notation introduced above, the spillover of the jth dye into the ith (secondary) detection channel, $S_{ij}$, is calculated as:

$$S_{ij} = \frac{MFI_{ij}}{MFI_{jj}}, \qquad (4)$$

where $MFI_{ij}$ is the mean fluorescence intensity measured from a particle population stained with the jth dye in the ith (secondary) detector channel, and $MFI_{jj}$ is the mean fluorescence intensity measured from the same population in the jth (primary) detector channel.

The emission spectrum of a dye is a property of the dye itself; the relative proportion of a dye's total emission that falls within each detection channel (i.e., the inherent spillover) is a property of dye's emission spectrum. In principle, if fluorescence measurements in each detection channel were directly comparable, a dye's measured spillover would reflect the inherent spillover. However, signals from the photodetectors depend on the photodetector gains, which typically are adjustable and are set independently for each detection channel, and the fluorescence measurements from each detection channel are not directly comparable. For this reason, the empirically measured spillover values defined by equation (4) are dependent on the photodetector gains. Changes in the photodetector gains typically require repeating the experimental determination of the spillover values.

Calibrated Fluorescence Measurements

The measured fluorescence intensity of a dye, reported as MFI, is dependent on the photodetector gain. A gain-independent, calibrated measure of fluorescence intensity is defined, with reference to a reference material measured under the same instrument settings and conditions, as the ratio of the measured fluorescence intensity of the dye to the measured fluorescence intensity of the reference material, both measured in the same detector channel.

The calibrated mean fluorescence intensity in the ith detector channel of a particle population labeled with the jth dye, designated $ABD_{ij}$, is defined herein as:

$$ABD_{ij} = C_i \cdot \frac{MFI_{ij}}{MFI_{iref}}, \qquad (5)$$

where $MFI_{ij}$ is the mean fluorescence intensity in the ith detector channel of the particle population labeled with the jth dye, $MFI_{iref}$ is the mean fluorescence intensity in the ith detector channel of the reference material, and $C_i$ is a constant.

The values of the $C_i$, once assigned, are fixed, although the numeric values are arbitrary. For convenience, the $C_i$ may be chosen to reflect, or be proportional to, the average number of dye-labeled antibodies bound to each reference particle. For example, using the CD4$^+$ lymphocyte-based fluorescence-matched standard particles, it is convenient to set $C_i$=40,000, which is the average number of dye-labeled anti-CD4 antibodies bound per CD4$^+$ lymphocyte in fixed human blood. The constant $C_i$ provides a scale to the units of fluorescence emission measured in detector channel i. However, the absolute value is not a critical aspect of the invention, and another value of $C_i$ may be used. For example, $C_i$ may be set to 1, in which case the ABD value is the fluorescence measured on a scale where the mean fluorescence of the reference material is 1, or, equivalently, the ABD value is the fluorescence as a ratio of the reference fluorescence.

As long as both the dye-labeled particle population and the reference material are measured in the linear range of the photodetector, such that the photodetector output signal is proportional to the actual number of photons detected, the calibrated fluorescence of the dye-labeled particle population, expressed in ABD units, is not dependent on the photodetector gain. Changes in photodetector gain will result in changes in the measured fluorescence intensities from both the particle population and the reference population, but the ratio of the two will remain constant.

Reference Fluorescence Settings

The uncalibrated MFI measured from a population at a particular photodetector gain setting can be obtained from the calibrated mean fluorescence intensity by inverting equation (5) to obtain $$MFI_{ij} = \frac{ABD_{ij} \cdot MFI_{iref}}{C_i}. \tag{6}$$

Thus, an uncalibrated fluorescence measurement ($MFI_{ij}$), which is dependent on the photodetector gain settings, is obtained from a gain-independent, calibrated fluorescence measurement ($ABD_{ij}$) by multiplying with a scaling factor obtained from the fluorescence of the reference material measured under the given photodetector gain setting. The scaling factor for the ith photodetector, $$\frac{MFI_{iref}}{C_i}, \tag{7}$$

is herein designated the "reference fluorescence intensity", $RFI_i$.

The reference fluorescence intensity provides a convenient method of obtaining uncalibrated fluorescence intensities of a population of labeled particles for any given photodetector gain setting. The calibrated fluorescence intensity of the labeled particles need only be determined once. Furthermore, as the calibrated fluorescence intensity is photodetector gain independent, the calibrated fluorescence intensity can measured under any suitable photodetector gain setting, independent of the settings used in the final assay. After selecting a specific photodetector gain setting for an assay, the reference material is measured under the selected settings to obtain the RFI. The uncalibrated fluorescence intensity value of the dyed particles, which is specific for the selected photodetector gain setting, is then calculated from the previously determined calibrated fluorescence intensity and the RFI measured under the current conditions.

Gain-Independent Calibrated Spillover Values

The calibrated spillover of the jth dye into a secondary channel is defined herein as the ratio of the calibrated emission of the dye-labeled particle population in the secondary channel, measured in ABD units, to the calibrated emission in the primary channel, measured in ABD units, i.e., the ratio of the MFI of the dye-labeled particle population in the secondary channel to the MFI in the primary channel, both calibrated and expressed in ABD units. Thus, the calibrated spillover of the jth dye into the ith detector channel, $NS_{ij}$, is $$NS_{ij} = \frac{ABD_{ij}}{ABD_{jj}}, \tag{8}$$

where $ABD_{ij}$ is the calibrated mean fluorescence intensity measured from a particle population labeled with the jth dye in the ith (secondary) detector channel, and $ABD_{jj}$ is the calibrated mean fluorescence intensity measured from the particle population in the jth (primary) detector channel.

From the definitions of the calibrated spillover value and the reference fluorescence intensity, defined above, the calibrated spillover is related $$NS_{ij} = S_{ij} \cdot \frac{RFI_j}{RFI_i}. \tag{9}$$

Conversely, $$S_{ij} = NS_{ij} \cdot \frac{RFI_i}{RFI_j}. \tag{10}$$

The gain setting provides a scaling factor to convert between a measured fluorescence expressed in gain-independent normalized ABD units and expressed as a gain-dependent MFI. Gain settings are used herein for converting between a gain-dependent spillover value and a gain-independent calibrated spillover value.

Expressed in matrix form, wherein S is the n×n matrix of spillover coefficients, $S_{ij}$, NS is the n×n matrix of calibrated spillover coefficients, $NS_{ij}$, and RFI is an n×n matrix having reference fluorescence intensity value, $RFI_i$, on the ith diagonal element and zero on all off-diagonal elements, $$NS = RFI^{-1} \cdot S \cdot RFI \tag{11}$$

and $$S = RFI \cdot NS \cdot RFI^{-1}. \tag{12}$$

Instrument Setup

Using the methods of the present invention, instrument set-up will comprise one or more the following steps:
1. predetermination of calibrated spillover values for the fluorescent assay reagents;
2. selection of initial instrument settings, including photodetector gain settings;
3. measurement of reference materials fluorescence under the selected instrument settings;
4. adjustment of selected instrument settings;
5. calculation of gain-dependent uncalibrated spillover values; and
6. calculation of compensation for the selected instrument settings.

Steps 2 and 3 may be repeated to permit adjustment of the instrument settings following the initial measurements of reference material fluorescence. Each of these steps is described in more detail, below.

1. Predetermined Calibrated Emission and Spillover Values

Calibrated emission and spillover values for the fluorescent assay reagents are obtained, as described herein, by measuring the MFI of a reference material and of a dye-labeled population, such as a fluorescent-matched standard, in each detection channel under the same instrument settings. The calibrated values are calculated as described above.

Predetermined calibrated spillover values will typically be determined once for each reagent lot. The predetermined calibrated values are determined for a given instrument. If the instrument is reconfigured, such as by changing filter sets or lasers, the calibrated values should be redetermined.

2. Initial Instrument Settings

Initial instrument settings, including an initial set of photodetector gain settings, are chosen preferably as an approximation of the settings likely to be useful for the assay contemplated. The initial set may be default values stored in the instrument, estimated based on the expected fluorescence of the reagents used in the particular assay, or determined experimentally, possibly using data obtained in previously carried out experiments. Methods of selecting an initial set of photodetector gain settings are well known in the art.

3. Reference Material Fluorescence

Using the initial instrument settings, the mean fluorescence intensify (MFI) of the reference material is measured in each detector channel. These measurements are gain-dependent, uncalibrated measurements that represent the observed fluorescence from the reference material under the selected detector gain settings.

The MFI of the reference material in each detection channel is used to calculate uncalibrated emission and/or spillover values for each of the assay reagents based on the previously determined calibrated values. Only the gain-dependent reference material fluorescence needs to measured for determining uncalibrated values for the assay reagents based on previously determined calibrated values.

In preferred embodiments in which the reference material emits in each channel, the emissions of a reference material are measured in each detector channel simultaneously. In some embodiments in which the reference material comprises multiple populations, wherein each population emits in only a subset of the channels, the measurements of each population may be made separately. Using some instruments, such as a flow cytometer, the measurements may be made using a mixture of the reference material populations, and the separate populations distinguished by gating based on fluorescence and scatter properties of the population particles.

4. Adjustment of Initial Instrument Settings

The photodetector gain setting may be adjusted if the expected fluorescence of a cell population stained with the assay reagents would not be "on-scale" or within the instrument's dynamic range. The MFI of a cell-population stained with the dye-labeled assay reagent will be proportional to the MFI measured from the corresponding fluorescence-matched standard. This proportionality can be determined empirically, or can be estimated if the relative average number of dye molecules on a cell and on the standard are known. The MFI that would be measured from the fluorescence-matched standard under the selected instrument settings can be calculated from the predetermined calibrated fluorescence values determined for the fluorescence-matched standard (determined as part of the predetermined calibrated spillover values) and the fluorescence values of the reference materials measured under the selected instruments settings. The expected MFI of a cell-population stained with the dye-labeled assay reagent then is estimated from the calculated MFI of the fluorescence-matched standard. If the expected data will not fall within desired region of the data space, one or more photodetector gains can be adjusted. For example, when the data are displayed in a dot plot, it is desirable that the data from negative samples are not compressed against an axis. The photodetector gain can be increased to move the data away from the axis.

If one or more photodector gain settings are adjusted, the fluorescence of the reference material should be measured again under the current, adjusted instrument settings.

5. Calculation of Gain-Dependent Spillover Values

The gain-dependent spillover values are calculated from the predetermined calibrated spillover values and the gain settings, as described above. Only the gain-dependent reference material fluorescence needs to measured under the specific initial photodetector gain settings.

6. Calculation of Compensation

The compensation is calculated from the calculated gain-dependent spillover values. The compensation matrix is determined either by calculating the values in the spillover matrix and then inverting the spillover matrix to obtain the compensation matrix or, equivalently, by directly calculating the values in the compensation matrix. The compensation matrix preferably is stored in the instrument or software for subsequent use.

The compensation matrix may be recalculated following an adjustment of photodetector gain settings in the same manner as for the original photodetector gain settings, described above. After an adjustment of the photodetector gain settings, the fluorescence emissions from the reference material are measured. Only the emissions of the reference material corresponding to an adjusted photodetector needs to measured, although it typically will be convenient to re-measure emissions in all the photodetector channels simultaneously. An adjusted spillover matrix is calculated from the predetermined calibrated spillover values and the re-measured emissions from the reference material. An adjusted compensation matrix for the adjusted settings is calculated from the adjusted spillover matrix, as described above. The adjusted compensation matrix is stored in the instrument or software for subsequent use.

EXAMPLES

The following examples are set forth so as to provide one of ordinary skill in the art with a complete disclosure and description of how to make and use the present invention, and are not intended to limit the scope of what the inventors regard as their invention.

Example 1

Preparation of CD4$^+$ T cell Fluorescence-Matched Standards

The example describes the preparation of a preferred fluorescence-matched standards useful for measuring the spillover of a fluorescent dye. The standards comprise CD4$^+$ lymphocytes in fixed human blood, stained using fluorescently labeled CD4-specific antibodies.

Antibodies:

Preferred CD4-specific antibodies include those produced from clone SK3 and clone RPA-T4, both available from BD Biosciences (San Jose, Calif.) labeled with a variety of dye labels. In addition to dye-labeled formulations, these antibodies also are available both as purified antibody and labeled with biotin, either of which can be used to produce new antibody-dye conjugates. Examples of the antibody-dye conjugates available from BD Biosciences for these two antibodies are shown in the table, below.

Examples of Commercially Available CD4-Specific Antibodies

| Label | Clone | Clone |
| --- | --- | --- |
| Alexa Fluor ® 488 | RPA-T4 | |
| Alexa Fluor ® 647 | RPA-T4 | |
| Alexa Fluor ® 700 | RPA-T4 | |
| AmCyan | | SK3 |

| Label | Clone | Clone |
|---|---|---|
| APC | RPA-T4 | SK3 |
| APC-Cy™7 | RPA-T4 | SK3 |
| APC-H7 | RPA-T4 | SK3 |
| FITC | RPA-T4 | SK3 |
| Pacific Blue™ | RPA-T4 | |
| PE | RPA-T4 | SK3 |
| PE-Cy™5 | RPA-T4 | SK3 |
| PerCP | | SK3 |
| PerCP-Cy5.5 | | SK3 |
| V450 | RPA-T4 | |
| Purified | RPA-T4 | SK3 |
| Biotin | RPA-T4 | SK3 |

Fluorescence-matched standards for each dye used in an assay are created using the CD4-specific antibody-dye conjugates, each antibody-dye conjugate containing one of the dyes used to label the assay reagents and which corresponds to one of a detector channels. For example, if a an PE-labeled antibody specific for a cell-surface marker will be used in an assay, a preferred fluorescence-matched standard would consist of CD4+ lymphocytes in fixed human blood, stained using a PE-labeled CD4-specific antibody.

Cell-Surface Staining:

Samples (50-200 µL) of whole blood (preferably collected in EDTA) are stained with antibody-dye conjugate for 30-60 minutes in the dark at a dye-conjugate concentration of 1 µg or less per 0.1 ml of blood.

Following staining, 2 mL of 1×FACS™ Lysing Solution (BD Bioscience, San Jose, Calif.) are added to the sample, and samples are incubated and washed according to the manufacturer's protocol. The FACS™ Lysing Solution lyses erythrocytes and fixes lymphocytes. Following the final wash, the sample is re-suspended in 0.5 mL of wash buffer (0.5% BSA+0.1% NaN3 in PBS) or 0.5-2% paraformaldehyde in PBS and held at 4° C. until used.

It will be understood that the particular antibody-dye conjugate used and the specific reaction components and particular reaction conditions used can have an effect on the results obtained. Routine experimentation should be carried out to determine an optimal antibody-dye conjugate concentration, preferred reaction components, such as buffers or lyse solutions, and reaction conditions, including staining times and temperatures, to maximize the signal:noise of the stained cells. Such routine optimization of assay conditions is standard practice in the field of immunostaining-based assays.

Example 2

Substitution or Replacement of Reference Materials

It is expected that a new production lot of the reference material, or even a new reference material, may be needed to replace the originally formulated reference material, for example, when the old lot of reference material is was used up over time. The methods of the present invention enable replacing an old reference material with a new reference material with minimal effort.

The fluorescence emissions of the reference material, measured using the current instrument settings, are used to calculate uncalibrated emission and/or spillover values for the assay reagents from the previously determined calibrated values. Because these previously determined calibrated values were calibrated using the fluorescence of the old reference material, the calculation of uncalibrated emission and/or spillover values from the previously determined calibrated values requires a determination of the fluorescence of the old reference material. In the present methods, the fluorescence of the old reference material is obtained from the measured fluorescence of the new reference material. This is enabled by first calibrating the emissions of the new reference material against the emissions of the old reference material or, equivalently, by measuring the ratio of the emissions of the new reference material against the emission of the old reference material. This comparison of the new to old reference materials typically will be carried out at the time the new reference material is produced. The fluorescence intensities the new reference material and the old reference materials are measured under the same photodetector gain settings, but these can be any suitable photodetector settings.

Using the ratio of the emissions of the new reference material against the emission of the old reference material, the MFI of the old reference material in the ith detector channel, designated $MFI_{iref-old}$, is obtained then from the measured MFI of the new reference material in the ith detector channel, $MFI_{iref-new}$, by multiplying by the previously determined ratio:

$$MFI_{iref-old} = MFI_{iref-new} \cdot \left(\frac{MFI_{iref-old}}{MFI_{iref-new}}\right).$$

This calculated MFI of the old reference material is then used to calculate uncalibrated emission and/or spillover values for the assay reagents from their previously determined calibrated values, as described above. Calibrated spillover values can be obtained similarly adjustment.

Alternatively, the calibrated fluorescence values of the reagents, calibrated with respect to the old reference material, can be adjusted to represent values calibrated with respect to the new reference material. The calibrated mean fluorescence intensity in the ith detector channel of a bead population labeled with the jth dye, designated $ABD^{new}_{ij}$, calibrated with respect to the new reference material, is related to the previously determined calibrated mean fluorescence intensity, designated $ABD_{ij}$, calibrated with respect to the old reference material, as follows:

$$ABD^{new}_{ij} = C_i \cdot \frac{MFI_{ij}}{MFI_{iref-new}},$$

$$= C_i \cdot \frac{MFI_{ij}}{MFI_{iref-old}} \cdot \frac{MFI_{iref-old}}{MFI_{iref-new}}$$

$$= ABD_{ij} \cdot \left(\frac{MFI_{iref-old}}{MFI_{iref-new}}\right),$$

where $MFI_{ij}$ is the mean fluorescence intensity in the ith detector channel of the bead population labeled with the jth dye, $MFI_{iref-new}$ is the mean fluorescence intensity in the ith detector channel of the new reference material, $MFI_{iref-old}$ is the mean fluorescence intensity in the ith detector channel of the old reference material, and $C_i$ is the constant for detector channel i assigned for use with the old reference material, or, equivalently, $$= ABD_{ij} \cdot \frac{C_i}{ADB_{iref-new/iref-old}},$$

where $ABD_{iref\text{-}new/iref\text{-}old}$ is the calibrated fluorescence of the new reference material, calibrated relative to the old reference material.

Equivalently, a calibrated fluorescence value, calibrated against the new reference material, is equal to the calibrated fluorescence value, calibrated against the old reference material, multiplied by the ratio of the reference fluorescence intensity of the old reference material to the reference intensity of the new reference material, i.e., $$\left(\frac{RFI_{i\text{-}old}}{RFI_{i\text{-}new}}\right).$$

Calibrated spillover values can be obtained similarly adjustment.

We claim:

1. A method for determining, in an instrument for analyzing a multiplicity of fluorescent dyes using a multiplicity of detector channels, a compensation value for the photodetector gain settings from an uncalibrated spillover value of a fluorescent dye that emits in a primary detection channel and a secondary detection channel, wherein the method comprises:
   a) performing a first set of measurements, in the primary and secondary detection channels of the fluorescent dye, of emissions of the fluorescent dye and a fluorescent reference material that emits in the primary and secondary detection channels of the fluorescent dye to obtain a first set of reference values associated with a first set of signal amplification settings on the instrument;
   b) adjusting the instrument to a second set of signal amplification settings;
   c) performing a second set of measurements, in the primary and secondary detection channels of the fluorescent dye, of emissions of the fluorescent dye and the reference material to obtain a second set of reference values associated with the second set of signal amplification settings;
   d) calculating a calibrated spillover value from the first set of reference values and determining the uncalibrated spillover value from the calibrated spillover value and the second set of reference values, wherein the uncalibrated spillover value is dependent on the second set of signal amplification settings and the calibrated spillover value is independent of the second set of signal amplification settings; and
   e) determining the compensation value from the uncalibrated spillover value of the fluorescent dye.

2. The method of claim 1, wherein said measurements of emissions from said fluorescent dye are carried out using a fluorescence-matched standard.

3. The method of claim 2, wherein said fluorescence matched standard comprises particles labeled with said fluorescent dye.

4. The method of claim 3, wherein said fluorescence matched standard comprises hard-dyed particles, labeled with said fluorescent dye.

5. The method of claim 2, wherein said fluorescence matched standard comprises cells in a sample of blood, wherein said cells are stained with an antibody labeled with said fluorescent dye.

6. The method of claim 5, wherein said cells are CD4+ lymphocytes in a sample of fixed human blood, and said antibody binds to CD4.

7. The method of claim 1, wherein said reference material consists of microparticles labeled with a plurality of fluorescent dyes.

8. The method of claim 1, wherein said instrument is a flow cytometer.

9. The method of claim 1, wherein the calculation of the calibrated spillover value is performed by multiplying the ratio of the emissions of the fluorescent dye measured in the primary and secondary detection channels by the ratio of the emissions of the reference material measured in the primary and secondary detection channels.

10. The method of claim 1, wherein the calculation of the calibrated spillover value is performed by multiplying the ratio of the emissions measured in the primary detection channel by the ratio of the emissions measured in the secondary detection channel.

11. The method of claim 1, wherein determining the uncalibrated spillover value is performed by multiplying the calibrated spillover value by the second set of reference values.

* * * * *